(12) United States Patent
Yakovlev

(10) Patent No.: US 9,254,340 B2
(45) Date of Patent: Feb. 9, 2016

(54) NANODIAMOND AND GLYCINE CONJUGATE AND METHOD FOR THE PREPARATION THEREOF

(75) Inventor: Ruslan Jur'evich Yakovlev, Moscow (RU)

(73) Assignee: Zakrytoe Aktsionemoe Obschestvo "Almaz Pharm", Moscow (RU)

( * ) Notice: Subject to any disclaimer, the term of this patent is extended or adjusted under 35 U.S.C. 154(b) by 96 days.

(21) Appl. No.: 14/234,137

(22) PCT Filed: Jul. 26, 2011

(86) PCT No.: PCT/RU2011/000490
§ 371 (c)(1),
(2), (4) Date: Jan. 21, 2014

(87) PCT Pub. No.: WO2013/015702
PCT Pub. Date: Jan. 31, 2013

(65) Prior Publication Data
US 2014/0162066 A1    Jun. 12, 2014

(51) Int. Cl.
*A61K 47/48* (2006.01)
*B82Y 5/00* (2011.01)

(52) U.S. Cl.
CPC ..... *A61K 47/48884* (2013.01); *A61K 47/48015* (2013.01); *A61K 47/48861* (2013.01); *A61K 47/48869* (2013.01); *B82Y 5/00* (2013.01); *Y10T 428/2982* (2015.01)

(58) Field of Classification Search
CPC ............... A61K 47/48884; A61K 47/48015; A61K 47/48861; A61K 47/48869; Y10T 428/2982; B82Y 5/00

USPC .................... 428/402; 562/498; 977/906, 896
See application file for complete search history.

(56) References Cited

U.S. PATENT DOCUMENTS

| 4,160,746 | A  | * | 7/1979  | Rashkin ..................... 502/306 |
| 7,569,205 | B1 | * | 8/2009  | Hens et al. ................... 423/446 |
| 7,820,130 | B2 | * | 10/2010 | Khabashesku et al. ....... 423/446 |
| 2005/0158549 | A1 |   | 7/2005 | Khabashesku et al. |
| 2014/0328920 | A1 | * | 11/2014 | Yakovlev ..................... 424/489 |

OTHER PUBLICATIONS

Y. Liu, Zh. Gu, J.L. Margrave, V.N. Khabashesku. Functionalization of Nanoscale Diamond Powder: Fluoro-, Alkyl-, Amino-, and Amino Acid-Nanodiamond Derivatives // Chem. Mater. 2004. V.16. pp. 3924-3930.
Russian Encyclopedia of Job Safety. 3 volumes. 2nd edition. Revised and enlarged edition, V. 3. M: pub. NTs ENAS. 2007, p. 181.
T.I. Shalina, L.S. Vasilyeva. General Issues of the Toxic Effect of Fluorine. // Siberian Medical Journal. 2009. #5, pp. 5-9.
Electron and Ion Solid-State Spectroscopy. /Edited by L.I. Firmens et al.—M. 1981, pp. 195-232.

* cited by examiner

*Primary Examiner* — Leszek Kiliman
(74) *Attorney, Agent, or Firm* — John Alumit

(57) ABSTRACT

The invention relates to the field of pharmaceutics and medicine and concerns a nano-diamond conjugate with glycine for delivering glycine into an organism, the conjugate comprising nano-diamond particles modified by glycine, with a particle size of 2-10 nm, and containing up to 21% by mass of glycine which is included in the composition of the superficial shell of said particles with a thickness of up to 1 nm, and to a method for producing said conjugate.

4 Claims, 10 Drawing Sheets

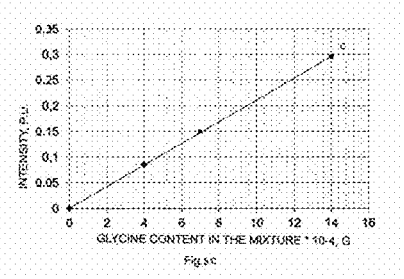

Figure 1:
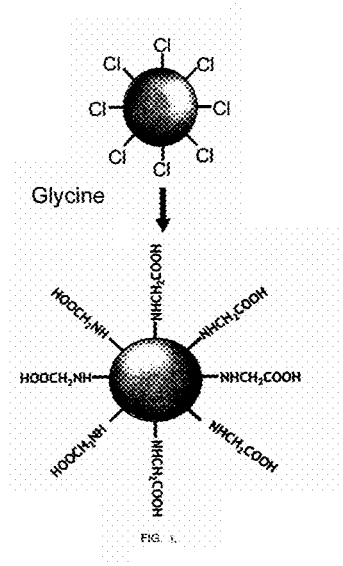

NANODIAMOND AND GLYCINE CONJUGATE AND METHOD FOR THE PREPARATION THEREOF

CROSS-REFERENCE TO RELATED APPLICATION

This application is a national stage application and claims the benefit of the priority filing date in PCT/RU2011/000490 referenced in WIPO Publication WO2013/015702 filed on Jul. 26, 2011. The earliest priority date claimed is Jul. 26, 2011.

FEDERALLY SPONSORED RESEARCH

Not Applicable

SEQUENCE LISTING OR PROGRAM

Not Applicable

BACKGROUND

The present invention relates to the field of pharmaceutics and medicine, in particular, to pharmaceutical nanotechnology, and is directed to a nanodiamond and glycine conjugate for the delivery of glycine into an organism, and to a method for the preparation of said conjugate.

A nanodiamond and glycine conjugate, comprised of particles 2-10 nm in size and used as a binding agent in polymeric compositions, is known in the art [1, 2]. A distinct feature of said conjugate is the presence of fluorine atoms on the nanodiamond's surface. The content of fluorine atoms on the nanodiamond's surface is less than 1%. However, in reality, the fluorine content can reach 14% or more.

A method for the preparation of nanodiamond and glycine conjugates used as binding agents in epoxy polymer composites of anti-corrosion coatings is also known in the art [2] and comprises the following: A nanodiamond sample is carefully weighed, placed in a reactor with a constant helium flow, and annealed at 150-470° C. for 3-4 hours. The nanodiamond samples are then fluorinated at 50-500° C. for 1-24 hrs by placing them in contact with a mixture of fluorine in hydrogen gases. To prepare a nanodiamond and glycine conjugate, the fluorinated nanodiamond is treated with ultrasound in o-dichlorobenzene for 20-30 minutes and combined with glycine ethyl ester hydrochloride ($NH_2CH_2COOCH_2CH_3 \cdot HCl$) and several drops of pyridine. The resulting mixture is stirred at 130-140° C. for 8-12 hours. The formed conjugate is washed with ethanol and dried in a vacuum at 70° C.

Fluorine-modified nanodiamond-glycine conjugates are undesirable for medical use, as the presence of fluorine and its derivatives in organic substances is known to increase their toxicity and can alter the microsomal system of the xenobiotic biotransformation indicators in the liver [3]. In addition, fluorine and fluorine compounds can accumulate in various environmental objects, where they can be present in different amounts [4].

SUMMARY

The present invention describes a nanodiamond and glycine conjugate for the delivery of glycine into an organism consisting of glycine-modified nanodiamond particles, 2-10 nm in size, and comprising up to 21±3 wt % of glycine incorporated into the surface membrane of the conjugate, wherein said surface membrane is up to 1 nm thick.

The amount of glycine in the nanodiamond and glycine conjugate is determined as follows: Nanodiamond combinations comprising various glycine amounts are prepared. Samples of each mixture and of the analyte are then taken in equal amounts. IR-spectra thereof are registered, and the most intensive characteristic signals, corresponding to the IR-spectra of the original glycine, are selected. Calibration curves of the IR-spectrum signal intensity while glycine content in the sample are plotted. The obtained calibration curves are then used to quantitatively determine the content of glycine in the analyzed nanodiamond-glycine conjugate by the intensity of the selected characteristic bands thereof. The obtained data is used to determine the average glycine content in the nanodiamond-glycine conjugate.

The present invention also describes a method for the preparation of the nanodiamond-glycine conjugate (the reaction scheme is represented on FIG. 1) with particle sizes of 2-10 nm, comprising up to 21±3 wt % of glycine, with the surface membrane thickness of up to 1 nm, wherein chlorine-modified nanodiamond particles with particle sizes of 2-20 nm are dissolved in a polar solvent to form a suspension, to which tertiary amine and glycine are added, and the resulting mixture is then treated with ultrasound, followed by keeping the mixture at 50-80° C. with subsequent centrifuging, washing with the solvent, and drying.

Triethylamine is used as the tertiary amine; pyridine, lower aliphatic alcohols, water-alcohol mixture, or water is used as the polar solvent. The ultrasound treatment is conducted for 5-60 min., and the mixture is kept at 50-80° C. for 18 to 48 hours.

Thus, preparation of nanodiamond-glycine conjugates with no fluorine atom content that exhibit improved dispersion ability and reduced ecological and endoecological damage, as well as simplification and cost reduction of the nanodiamond-glycine conjugate preparation process prove to be important and practically relevant tasks.

DRAWINGS

FIG. 1. Preparation scheme for the nanodiamond-glycine conjugate.

Figure 2:

FIG. 2. Photomicrograph of the described nanodiamond-glycine conjugate.

Figure 3:
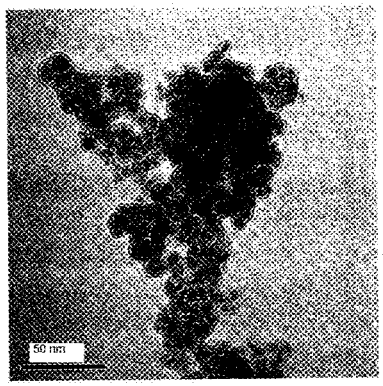

FIG. 3. Photomicrograph of the described nanodiamond-glycine conjugate.

Figure 4:
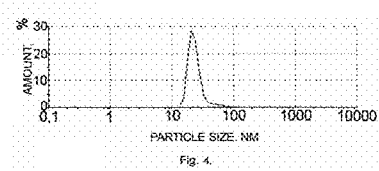

FIG. 4. Size distribution of the described nanodiamond-glycine conjugate in suspension.

Figure 5:
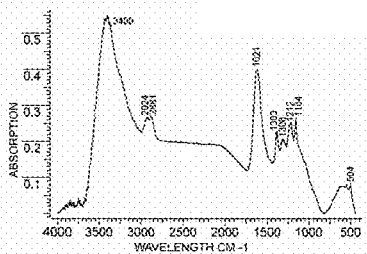
Figure 4:
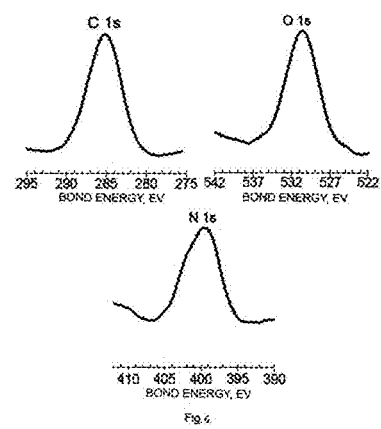

FIG. 5. IR-spectrum of the described nanodiamond-glycine conjugate.

FIG. 6. C 1s, O 1s, N 1s XPE-spectra of the surface of the described nanodiamond-glycine conjugate.

Figure 7:
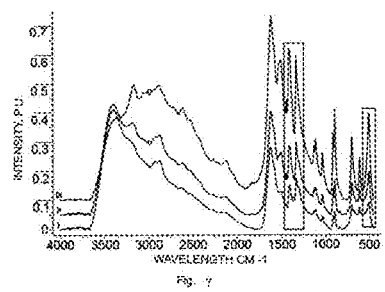

FIG. 7. IR-spectra of the nanodiamond and glycine mixtures for plotting calibration curves. I, II, III are the spectra of mixtures comprising the following ratio of glycine wherein, relative to each other, respectively: 1:1.75:2.5. Characteristic peaks are outlined.

Figure 8A:
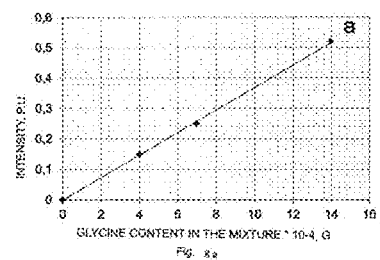
Figure 8B:
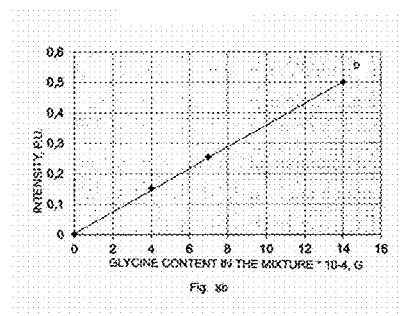

FIG. 8 Calibration curves for each characteristic band in the IR-spectra of the nanodiamond-glycine mixture. a, b, c—are calibration curves for the 1,407, 1,332, and 504 $cm^{-1}$ bands, respectively.

Figure 9:
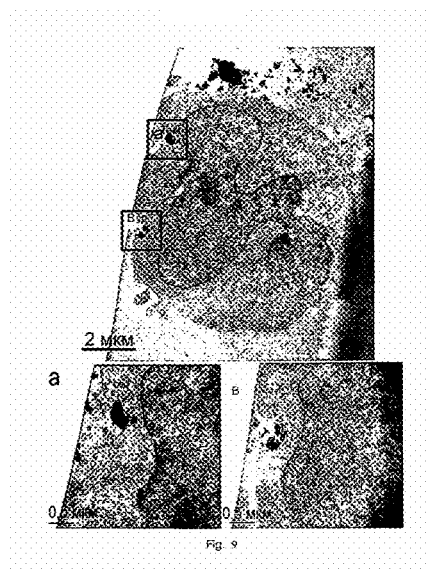

FIG. 9. Photomicrograph of the nanodiamond-glycine conjugate's penetration into the lymphoblast MOLT-4 cell; a and b—are the areas of particle penetration into cells.

DESCRIPTION

The claimed nanodiamond-glycine conjugate with no fluorine atom on the surface thereof is an ultradisperse powder, dark grey or dark grey with either a greenish or a dark blue tint and particle sizes of 2 to 10 nm (FIG. 2), wherein the size of the aggregates thereof in an aqueous suspension is 25 to 50 nm (FIG. 4).

FIG. 2 clearly demonstrates that the claimed conjugate has an ultradisperse structure created by particles with a diameter smaller than resolution ability of the used instrument (from 20 nm).

Photomicrographs of the nanodiamond-glycine conjugate particles are obtained on a super-high resolution auto emission scanning electron microscope Zeiss Ultra Plus (Carl Zeiss, Germany). The conditions of the film taking are cited on the photomicrograph.

FIG. 3 demonstrates that the nanodiamond-glycine conjugate particle size distribution is 2-10 nm, and the surface membrane thickness is up to 1 nm. Photomicrographs of the nanodiamond-glycine conjugate particles were obtained on a transmission electron microscope Jeol 1011 (JEOL, Japan).

FIG. 4 shows a distribution curve of particle sizes in the suspension of the claimed nanodiamond-glycine conjugate that shows particle sizes in the suspension being 25-50 nm. Distribution of particle sizes in the conjugate suspension is determined by laser dynamic light scattering on a ZetaSizer instrument (Malvem Instruments, USA). The X-axis is the logarithmic scale of the particles in nm. The Y-axis is the percent composition.

FIG. 5 shows an IR-spectrum of the claimed conjugate. The spectrum shows a broad intense band with a maximum at 3,400 cm$^{-1}$; a strong signal at 1,621 cm$^{-1}$; six bands of medium intensity at 2,924, 2,881, 1,383, 1,306, 1,212, and 1,154 cm$^{-1}$; and a weak characteristic signal at 504 cm$^{-1}$. The spectrum has maximums at 1,383; 1,306; 1,212; and 1,154 cm$^{-1}$; corresponding to the maximums of the original glycine amino acid, which shifted into the 1,400-1,100 cm$^{-1}$ region because of the covalent bond formation with the nanodiamond surface.

IR-spectra were registered on a FTIRS IR200 Thermonicolet instrument (Thermo Scientific, USA). Resolution–2 cm$^{-1}$·number of scans–64. For the analysis, carefully weighed samples were mixed with KBr powder and pressed into tablets.

FIG. 6 shows XPE-spectra of the claimed nanodiamond-glycine conjugate. Said X-ray photoelectron spectra define the nature, energy condition, and number of surface atoms of nanodiamond particles and identify practically all the elements, except for hydrogen and helium [5].

The surface of the claimed nanodiamond-glycine conjugate is examined on a LAS-3000 instrument (Riber, France) equipped with a hemispherical analyzer OPX-150. The non-monochromatized X-ray radiation from an aluminum anode (A1a=1486.6 eV) (12 kV voltage on the tube and 20 mA emission current) is used for photoelectron excitation. Calibration of the photoelectron peaks is conducted along the C 1s carbon line with binding energy of 285 eV ($E_b$). Vacuum in the work chamber is 6.7×10$^{-8}$ Pa. High vacuum is achieved with an ion pump.

The elemental composition on the surface of the claimed nanodiamond-glycine conjugate according to the XPE data is shown in Table 1.

TABLE 1

Elemental composition and surface atom-binding energy of the claimed nanodiamond-glycine conjugate.

| Name of the Characteristics | Chemical Elements | | |
|---|---|---|---|
| | C | O | N |
| At % | 77.5-94.5 | 4-14 | 1.5-8.5 |
| Binding energy, eV | 285.2 ± 0.5 | 530.7 ± 0.5 | 399.8 ± 0.5 |

Table 1 demonstrates that the claimed nanodiamond-glycine conjugate does not contain fluorine or any other halogen atoms in the amounts exceeding the instrument error (0.1 at %) since in the process of the nanodiamond-glycine conjugate's formation (FIG. 1), all chlorine atoms are substituted with glycine molecules and leave the nanodiamond surface as HCl molecules.

Chlorine-modified nanodiamond particles used in the preparation method are obtained by annealing the nanodiamond at 2-3 L/hr. and 500-1,200° C. in a H$_2$ gas stream for 1-8 hours. The annealed nanodiamond is then chlorinated in liquid phase with molecular chlorine. For that, chlorine obtained in the reaction between K$_2$Cr$_2$O$_7$ (or KMnO$_4$) and hydrochloric acid is dissolved in CCl$_4$ to 3-5 wt %. Chlorination is conducted under photochemical exposure to visible light for 36 to 60 hours at 50-70° C. The sample is then washed with CCl$_4$, the suspension is centrifuged at 6,000 rpm, and dried in a vacuum to constant weight.

More precisely, the preparation of the nanodiamond-glycine conjugate comprises preparing a chlorinated nanodiamond suspension in a polar organic solvent, water-organic solvent, or in water, wherein glycine, as amino acetic acid NH$_2$CH$_2$COOH, and tertiary amine are then added to said suspension. Organic solvents that dissolve glycine, such as pyridine or lower aliphatic alcohols, are preferred. The obtained mixture is treated with ultrasound (50 W) for 5-60 min., and kept at 50-80° C. with constant stirring for 12-48 hrs. The resulting product is washed with ethanol, centrifuged, and the residue is dried in a vacuum overnight at 70° C.

Thus, in the claimed method for the preparation of the nanodiamond-glycine conjugate, the hazardous, complicated, and expensive process of fluorination with fluorine gas is replaced by the readily available, safe, and substantially less expensive process of chlorination in liquid phase, while the expensive glycine derivative, glycine ethyl ester hydrochloride, is replaced by a significantly less expensive amino acid, glycine.

The claimed nanodiamond-glycine conjugate dos not contain fluorine atoms, and the dispersion ability of the particles thereof in a suspension is increased 6-12 times The obtained nanodiamond-glycine conjugate may be useful in medicine as a system for the delivery of glycine into an organism. For that purpose, electron microscopy is used to study the interaction between the obtained conjugate and the cellular culture by cellular biology methods.

The invention is illustrated by the following example:

EXAMPLE

A 300 mg sample of nanodiamond is annealed in a gaseous H$_2$ stream at 3.0 L/hr. and 1,000° C. for 6 hrs. The annealed nanodiamond is then subjected to liquid-phase chlorination with molecular chlorine dissolved in 40 ml of CCl$_4$ to 6 at % of Cl$_2$. Chlorination is conducted under photochemical exposure to visible light for 60 hours at 60° C. The sample is then washed with $CCl_4$, the suspension is centrifuged at 6,000 rpm and dried under 0.1 mm Hg to constant weight. The chlorinated nanodiamond is then suspended in 40 ml of water-alcohol mixture (water:alcohol=1:1), combined with 300 mg of glycine as free amino acid $NH_2CH_2COOH$ and 1 ml of triethylamine. The resulting mixture is treated with ultrasound (50 W) for 60 minutes and kept at 65° C. with constant stirring for 30 hours. The resulting product is washed with large amounts of ethanol, centrifuged, and dried in a vacuum at 70° C. overnight. The residual moisture content of the product is 2.2%. The yield of the final product is 279 mg (93%).

The obtained product is an ultradisperse powder, dark grey with a bluish tint, with 2-10 nm primary particle sizes and a surface layer membrane measuring up to 1 nm; said product is characterized by IR-spectroscopy: a broad intense band at 3,400 $cm^{-1}$, a strong signal at 1,621 $cm^{-1}$, six moderately intense bands at 2,924, 2,881, 1,383, 1,306, 1,212, and 1,154 $cm^{-1}$, and a weak signal at 504 $cm^{-1}$. The particle size in the suspension of the obtained product is 25 nm. The elemental composition of the surface is shown in Table 3.

TABLE 3

XPE-data on the obtained product.

| Name of the Characteristics | Chemical Elements | | |
|---|---|---|---|
| | C | O | N |
| At % | 80.1 ± 0.1 | 11.5 ± 0.1 | 8.4 ± 0.1 |
| Binding energy, eV | 285.2 ± 0.5 | 530.7 ± 0.5 | 399.8 ± 0.5 |

To determine the mass fraction of glycine in the obtained conjugate, three nanodiamond-glycine mixtures are prepared in a 1:1.75:3.5 ratio, respectively. A 0.0035 g sample of each mixture is triturated in a mortar with 0.09 g KBr. Next, 0.70 g of the obtained mixture is pressed into a tablet and subjected to IR spectroscopy (FIG. 7). Characteristic bands are selected at 1,407, 1,332, and 504 $cm^{-1}$, respectively, and calibration graphs are then plotted therefore (FIG. 8). Characteristic band intensities on the IR-spectrum of the obtained nanodiamond-glycine conjugate sample weighing 0.0035 g are 0.23, 0.22, and 0.10 p.u., respectively. Calibration curves a, b, and c (FIG. 8) are used to determine the glycine content in the sample, which constitutes 0.00057±8·$10^{-5}$ g of glycine in the sample. The mass fraction of glycine in the sample is therefore 21±3 wt %.

Ultrasound treatment of the suspension for 30-60 minutes, followed by keeping said suspension at 70-80° C. for 30-48 hours, and using pyridine or lower aliphatic alcohols as polar solvents, produce a conjugate with the analogous characteristics and glycine content in the 13-21 wt range.

Ultrasound treatment of the suspension for 5-30 minutes, followed by keeping said suspension at 50-70° C. for 12-30 hours, and using water-alcohol mixtures or water as polar solvents produce a conjugate with the analogous characteristics and glycine content in the 2-14 wt % range.

The obtained nanodiamond-glycine conjugate is used for the delivery of glycine into an organism. The presence of the nanodiamond and glycine conjugate in an organism is confirmed by electron microscopy in the reaction thereof with the lymphoblast MOLT-4 cell culture (FIG. 9) after an eight-hour incubation. FIG. 9 demonstrates that the conjugate causes invagination of the lymphoblast's cellular membrane, which, while gradually penetrating deeper, leads to the absorption of the nanodiamond-glycine conjugate by the cell.

Cellular sections incubated with the obtained conjugate are prepared on a Leica Ultracut UCT ultramicrotome (Leica, Germany). Photomicrographs of cellular sections are prepared on a transmission electron microscope Jeol 1011 (JEOL, Japan).

REFERENCES 1. 1. USP at 2005/0158549 A1, Jul. 21, 2005.
2. 2. Y. Liu, Zh. Gu, J. L. Margrave, V. N. Khabashesku. Functionalization of Nanoscale Diamond Powder: Fluoro-, Alkyl-, Amino-, and Amino Acid-Nanodiamond Derivatives//Chem. Mater. 2004. V.16. p.p. 3924-3930.
3. Russian Encyclopedia of Job Safety. 3 volumes. $2^{nd}$ edition. Revised and enlarged edition, V. 3. M: pub. NTs ENAS. 2007, p. 181.
4. T. I. Shalina, L. S. Vasilyeva. General Issues of the Toxic Effect of Fluorine.//Siberian Medical Journal. 2009. #5, p.p. 5-9.
5. Electron and Ion Solid-State Spectroscopy./Edited by L. I. Firmens et al.—M. 1981, p.p. 195-232.

What is claimed:

1. A nanodiamond-glycine conjugate for the delivery of glycine into an organism, said conjugate consisting essentially of glycine-modified nanodiamond particles, said particles comprising up to 21±3 wt % of the glycine, said glycine is part of a shell surface coating having a thickness of up to 1 nm.

2. A method of preparation of nanodiamond-glycine conjugate for delivery of glycine into an organism, said nanodiamond-glycine conjugate consisting essentially of glycine-modified nanodiamond particles comprising up to 21±3 wt % of the glycine, said glycine is part of a shell surface coating having a thickness of up to 1 nm, said method comprising the steps of:
   dissolving in the mixture chlorine-modified nanodiamond particles having a particle size ranging from 2 to 10 nm in a polar solvent to yield a suspension,
   adding to the mixture tertiary amine and glycine,
   treating the mixture with ultrasound and then maintaining the mixture at a temperature of 50-80° C.,
   spinning the treated mixture in a centrifuge,
   washing the mixture with a solvent and receiving a residue, and
   drying the residue.

3. The method according to claim 2, wherein said ultrasound treatment is conducted for 5-60 minutes and said mixture is maintained at a temperature of 50-80° C. for 12-48 hours.

4. The method according to claim 2, wherein said tertiary amine is triethylamine, and said polar solvent is selected from at least one of pyridine, lower aliphatic alcohol, water-alcohol mixture, or water.

* * * * *